(12) United States Patent
Beiriger (10) Patent No.: US 8,529,491 B2
(45) Date of Patent: Sep. 10, 2013

(54) DETECTING BLOOD FLOW DEGRADATION

(75) Inventor: Michael James Beiriger, Pittsburgh, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 773 days.

(21) Appl. No.: 12/650,745

(22) Filed: Dec. 31, 2009

(65) Prior Publication Data
US 2011/0160637 A1    Jun. 30, 2011

(51) Int. Cl.
*A61M 5/00*    (2006.01)

(52) U.S. Cl.
USPC .............................. 604/8; 210/646; 73/335.03

(58) Field of Classification Search
USPC .................... 604/4.01, 5.01, 6.06, 6.07, 6.09, 604/6.1, 6.11, 6.16; 210/645–647, 767
See application file for complete search history.

(56) References Cited

U.S. PATENT DOCUMENTS

| | | |
|---|---|---|
| 4,898,576 A | 2/1990 | Philip |
| 5,438,510 A | 8/1995 | Bryant et al. |
| 6,210,591 B1 | 4/2001 | Krivitski |
| 6,299,583 B1 * | 10/2001 | Eggers et al. ................. 600/526 |
| 6,406,631 B1 | 6/2002 | Collins et al. |
| 6,503,062 B1 | 1/2003 | Gray et al. |
| 6,730,233 B2 | 5/2004 | Pedrazzi |
| 6,814,864 B1 | 11/2004 | Favre et al. |
| 6,821,441 B2 | 11/2004 | Pedrini et al. |
| 6,973,373 B2 | 12/2005 | Gray et al. |
| 7,083,719 B2 | 8/2006 | Bowman et al. |
| 7,255,680 B1 | 8/2007 | Gharib |
| 7,273,465 B2 | 9/2007 | Ash |
| 7,766,873 B2 | 8/2010 | Moberg et al. |
| 2001/0021817 A1 * | 9/2001 | Brugger et al. ............... 604/6.11 |
| 2004/0154967 A1 | 8/2004 | Pedrazzi |
| 2005/0251086 A1 | 11/2005 | Sternby |
| 2005/0274658 A1 | 12/2005 | Rosenbaum et al. |
| 2007/0158247 A1 | 7/2007 | Carr et al. |
| 2007/0158268 A1 | 7/2007 | DeComo |
| 2008/0149563 A1 | 6/2008 | Ash |
| 2008/0177216 A1 | 7/2008 | Ash |
| 2008/0208011 A1 * | 8/2008 | Shuler .......................... 600/301 |
| 2009/0012442 A9 * | 1/2009 | Brugger et al. ............... 604/4.01 |
| 2010/0004589 A1 | 1/2010 | Hedmann et al. |

FOREIGN PATENT DOCUMENTS

| | | |
|---|---|---|
| DE | 4240681 | 6/1994 |
| EP | 0235591 | 9/1987 |
| GB | 2 424 966 | 10/2006 |
| JP | 02289259 | 11/1990 |
| JP | 2002095741 | 4/2002 |
| JP | 2005218709 | 8/2005 |

OTHER PUBLICATIONS

Dietrich Polaschegg and Levin, *Hemodialysis Machines and Monitors*, Replacement of Renal Function by Dialysis, Fourth Edition, Chapter 14, pp. 334-379, 1996.

Dinesh Khullar, *Basic Fundamentals of Dialysis*, JIMSA, vol. 15, No. 3, pp. 163-169, Jul.-Sep. 2002.

(Continued)

*Primary Examiner* — Melanie Hand
(74) *Attorney, Agent, or Firm* — Fish & Richardson P.C.

(57) ABSTRACT

A method for detecting blood flow degradation in a dialysis system. The method includes measuring a flow rate of blood in a blood line, calculating a current impedance value based on the measured flow rate, and comparing the current impedance value to a baseline impedance value.

48 Claims, 5 Drawing Sheets

(56) References Cited

OTHER PUBLICATIONS

Wamsiedler et al., *Heparin-Free Dialysis with an On-Line Hemodiafiltration System*, Artificial Organs, 17(11) pp. 948-953, Feb. 1993.

Application from U.S. Appl. No. 12/408,353, filed Mar. 20, 2009.
International Search Report and Written Opinion; PCT/US2010/057581; mailed Mar. 15, 2011.

* cited by examiner

DETECTING BLOOD FLOW DEGRADATION

TECHNICAL FIELD

This invention relates to detecting blood flow degradation, and more particularly to detecting blood flow degradation based on hydraulic impedance of a blood circuit.

BACKGROUND

Some known extracorporeal blood treatment devices, such as hemodialysis machines, draw blood from a patient via a blood circuit, circulate the blood through a treatment unit of the blood circuit, and then return the treated blood to the patient via the blood circuit. This circulation of the blood outside the patient's body typically begins and ends with the passage of the blood through a single or dual lumen catheter system that is connected to the patient. The circulation of blood is generally assisted by a pump to increase the rate of blood flow, as well as to provide a regulated flow of blood throughout the treatment.

Sometimes a degradation in blood flow may occur, which may compromise treatment efficacy. Such blood flow degradation can be the result of an access blockage, such as a needle of the catheter system contacting a wall of a vein in which it is inserted and thereby inhibiting blood flow. Other blood flow degradation can result from a kinking or binding of blood circuit tubing and/or the formation of a clot. Clots may occur, for example, at an access point (i.e., a point at which the blood circuit connects to the patient) or within the blood circuit, such as at an input of the treatment unit.

SUMMARY

In general, this invention relates to detecting blood flow degradation, and more particularly to detecting blood flow degradation based on hydraulic impedance of a blood circuit.

One aspect of the invention features a method for detecting blood flow degradation in a dialysis system. The method includes measuring a flow rate of blood in a blood line, calculating a current impedance value based on the measured flow rate, and comparing the current impedance value to a baseline impedance value.

Another aspect of the invention provides a computer-readable medium having encoded thereon software for detecting blood flow degradation in a blood circuit. The software includes instructions for receiving information corresponding to measurement data from one or more sensors, calculating a current impedance value based on the measurement data, and comparing the current impedance value to a baseline impedance value.

In another aspect, the invention provides a dialysis system that includes a blood circuit including a blood pump and tubing for conveying blood between the blood pump and a patient. The dialysis system also includes one or more flow sensors for measuring a flow rate of blood within the tubing, and a controller in communication with the one or more flow sensors. The controller is configured to calculate a hydraulic impedance within the tubing based, at least in part, on signals received from the one or more sensors.

Implementations may include one or more of the following features.

The method can also include inferring blood flow degradation if the current impedance value differs from the baseline impedance value by more than a maximum limit.

In certain implementations, the method can include transmitting a signal corresponding to the measured flow rate to a controller, and utilizing the controller to calculate the current impedance value based on the measured flow rate.

The method can also include utilizing the controller to compare the current impedance value to the baseline impedance value.

In some implementations, the method can include alerting a user if the current impedance value differs from the baseline impedance value by more than a maximum limit. Alerting the user can include activating an alarm, such as an audible alarm or a visual alarm.

In certain implementations, alerting the user can include displaying information concerning a detected blood flow degradation on a display device. The displayed information can include information regarding a cause of blood flow degradation.

In some implementations, the displayed information includes information regarding a location of a cause of blood flow degradation relative to the dialysis system.

The method can also include administering a saline bolus if the current impedance value differs from the baseline impedance value by more than a maximum limit.

In some implementations, the saline bolus is automatically administered at the direction of a controller of the dialysis system.

The method can also include adjusting a needle at a patient access point if the current impedance value differs from the baseline impedance value by more than a maximum limit.

In some implementations, the method also includes un-kinking kinked tubing if the current impedance value differs from the baseline impedance value by more than a maximum limit.

In certain implementations, the method can include determining a cause of blood flow degradation indicated by the difference between the current impedance value and the baseline impedance value.

The method can also include determining a location of a cause of blood flow degradation based, at least in part, on the difference between the current impedance value and the baseline impedance value.

In some implementations, comparing the current impedance value to the baseline value comprises calculating a percent difference between the current impedance value and the baseline value.

In certain implementations, the method can include identifying a cause of blood flow degradation based on the calculated percent difference.

In some implementations, the software also includes instructions for calculating the baseline impedance value based, at least in part, on measurement data received from the one or more sensors.

In some implementations, the tubing includes an arterial line for conveying blood from a patient to the blood pump, and a venous line for conveying blood from the pump back to the patient.

In certain implementations the one or more flow sensors include an arterial flow sensor arranged to measure a flow rate of blood flowing within the arterial line. The controller is configured to calculate a hydraulic impedance within the arterial line based, at least in part, on signals received from the arterial flow sensor.

In some implementations, the one or more flow sensors include a venous flow sensor arranged to measure a flow rate of blood flowing within the venous line, and the controller is configured to calculate a hydraulic impedance within the venous line based, at least in part, on signals received from the venous flow sensor.

In certain implementations, the dialysis system also includes one or more pressure sensors for measuring pressure within the tubing, and the controller is in communication with the one or more sensors.

In some implementations, the controller is configured to compare the calculated hydraulic impedance to a baseline impedance value, and to detect a blood flow degradation based on the comparison.

The dialysis system can also include a display device in communication with the controller. The controller can be configured to display information concerning a detected blood flow degradation on the display device.

In certain implementations, the dialysis system includes an audible alarm, and the controller is configured to sound the audible alarm in response to detecting a blood flow degradation.

In some implementations, the controller is configured to control operation of the pump, and the controller is configured to halt operation of the pump in response to detecting a blood flow degradation.

The dialysis system can also include a saline source, a saline line connecting the saline source to the tubing, and a saline valve in electrical communication with the controller. The saline valve is operable to control a flow of saline from the saline source toward the tubing, and the controller is configured to administer a saline bolus, via operation of the saline valve, in response to detecting a blood flow degradation.

In certain implementations, the dialysis system also includes memory in communication with the controller.

In some implementations, the memory includes stored data corresponding to a baseline impedance value.

In certain implementations, the controller is configured to calculate a baseline impedance value based, at least in part, on signals received from the flow sensors, and to cause the baseline impedance value to be stored in the memory.

In some implementations, the blood pump includes dual chambers operable to circulate blood through the blood circuit.

The blood pump can be a pneumatically driven pump.

In some implementations, the blood pump is a peristaltic pump.

In certain implementations, the dialysis system also includes a pneumatic source and a directional control valve in fluid communication with the blood pump and the pneumatic source and in electrical communication with the controller. The controller can be configured to control operation of the blood pump via the directional control valve.

In some implementations, the dialysis system also includes a dialyzer, connected to the blood circuit, for separating waste from blood flowing within the blood circuit.

In certain implementations, the dialysis system includes a dialysate circuit through which dialysate flows.

In some implementations, the dialysis system includes a sorbent cartridge in fluid communication with the dialysate circuit. The sorbent cartridge is configured so that the dialysate can pass therethrough. The sorbent cartridge is adapted to remove one or more substances from the dialysate as the dialysate passes through the sorbent cartridge.

In certain implementations, the dialysis system is a hemodialysis system.

In some implementations, the dialysis system is a sorbent-based dialysis system.

Implementations can include one or more of the following advantages.

In some implementations, a characteristic hydraulic impedance of blood flow within a blood circuit can be determined and clots, occlusions, or changes in access flow rate can be inferred from the hydraulic impedance. Thus, relatively simple techniques for detecting clots, access blockage, and kinks in system tubing can be provided.

Detection and identification of degradation in blood flow through a blood circuit, e.g., of a hemodialysis system, can allow operators to correct these issues in order to maintain clearance. Early detection allows for early correction of an issue, and, as a result complications associated with blood flow degradation can be reduced.

In some implementations, the systems and/or methods can provide for identification of degradation of blood flow through a blood circuit, which can allow an operator to attempt to rectify the issue before treatment efficacy is compromised. This may provide the operator with an opportunity to continue effective treatment in circumstances where effective treatment may otherwise have been compromised or abandoned.

In some cases, the systems and/or methods can provide for automatic corrective or protective action in circumstances where a blood flow degradation issue is detected. For example, the systems may be configured to automatically deliver a saline bolus where a blood flow degradation issue is detected. Alternatively or additionally, systems can be configured to automatically halt operation of a blood pump when a blood flow degradation issue is detected.

Respective characteristic hydraulic impedances of blood flow within arterial and venous lines of a blood circuit can be determined and the relative location of a cause of blood flow degradation can be inferred from the detected hydraulic impedances.

In some embodiments, a cause of blood flow degradation (e.g., clot, occlusion, or access blockage) can be inferred based on magnitudes of the hydraulic impedances. Knowing the cause of blood flow degradation can help the system operator to select an appropriate way of addressing the issue.

Other aspects, features, and advantages are in the description, drawings, and claims.

DETAILED DESCRIPTION

A dialysis system, such as a hemodialysis system including an extracorporeal fluid circuit used in filtering blood from a patient, can be configured to use measured data, pertaining to blood flow and fluid pressure, to calculate a hydraulic impedance to blood flow of the dialysis system. As will be discussed in detail, the hydraulic impedance can be used for the detection and identification of blood flow degradation, and causes thereof, such as clots, occlusions, and access blockage, within the dialysis system. The detection and/or identification of a blood flow degradation can allow for correction of the blood flow degradation before treatment efficacy is compromised.

Figure 1:
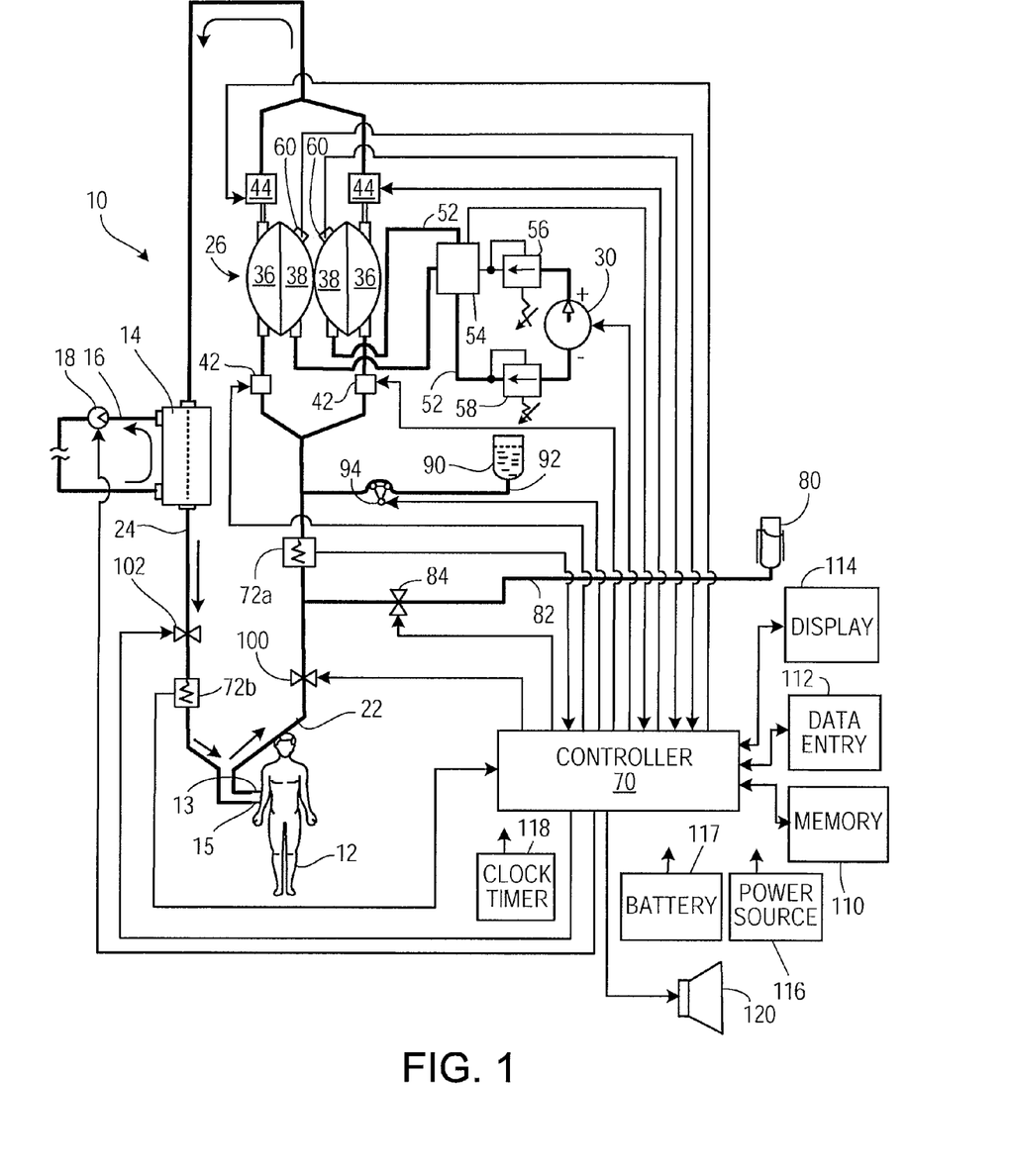
FIG. 1 is a schematic view of a dialysis system.

FIG. 1 illustrates a dialysis system 10 for the extracorporeal treatment of blood from a patient 12 whose kidney function is impaired. The dialysis system 10 includes a blood circuit 20 through which the patient's blood travels, a dialyzer 14 that separates wastes from the blood, and a dialysate circuit 16 through which dialysate flows carrying the separated waste away. The blood circuit 20 includes an arterial line 22 for withdrawing blood from the patient 12 and delivering it to the dialyzer 14 and a venous line 24 for returning treated blood to the patient 12.

Figure 2:
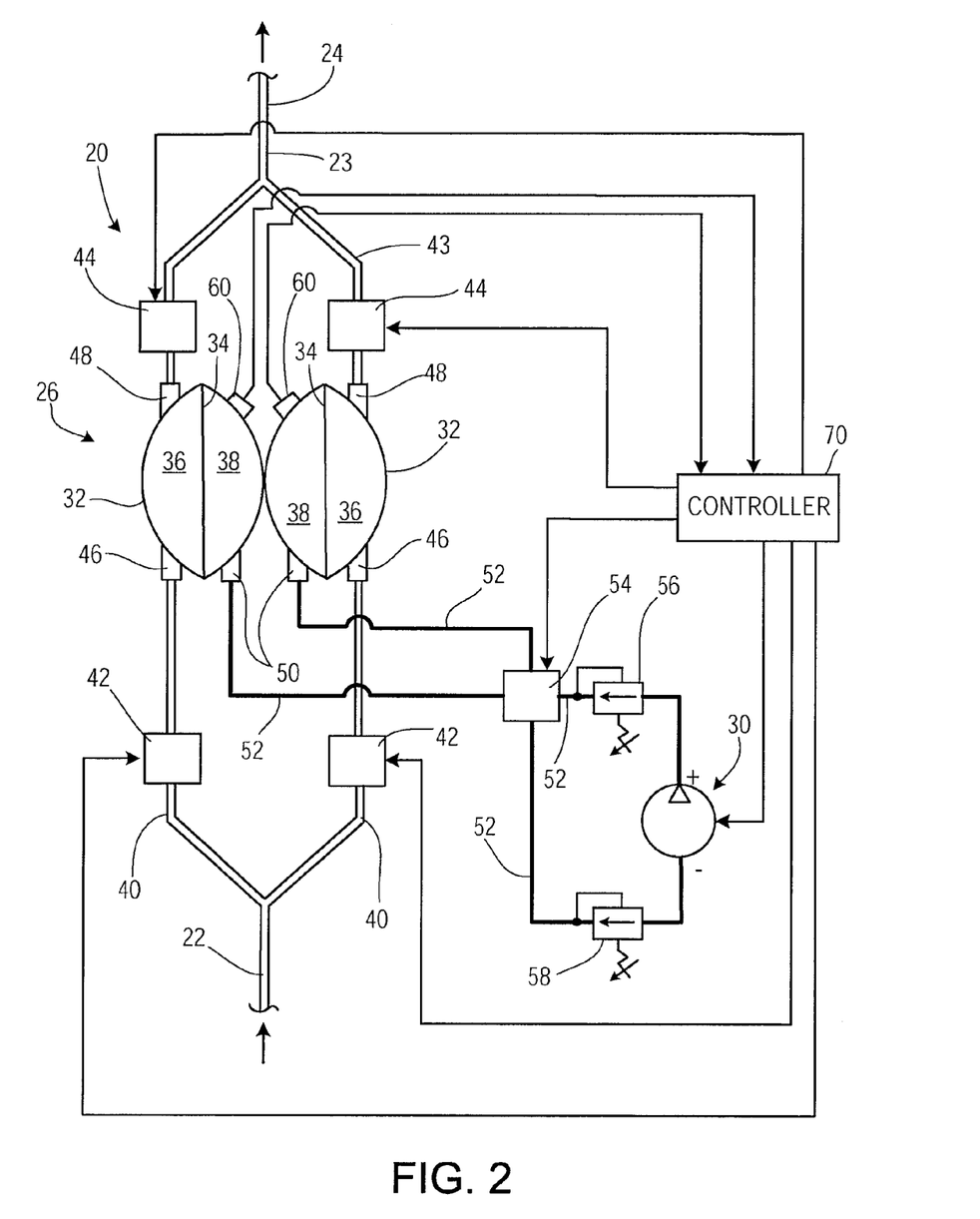
FIG. 2 is a schematic view of a dual chamber pump of the dialysis system of FIG. 1.

A dual chamber blood pump 26 drives the blood through the blood circuit 20. Referring to FIG. 2, the blood pump 26 defines two chambers 32, each of which contains a flexible membrane 34. Each flexible membrane 34 divides its respective chamber 32 into first and second pumping chambers 36, 38. A pair of arterial branch lines 40 with inlet valves 42 provide for fluid communication between the arterial line 22 and inlet ports 46 of the first pumping chambers 36. A pair of venous branch lines 43 with outlet valves 44 provide for fluid communication between outlet ports 48 of the first pumping chambers 36 and the venous line 24. Gaseous ports 50 at the second pumping chambers 38 communicate with a pneumatic pressure source 30 (e.g., a pneumatic pump) via pneumatic lines 52 and a directional control valve 54.

The pneumatic pressure source 30 drives the blood pump 26. In this regard, the pneumatic pressure source 30 supplies the blood pump 26 with both vacuum pressure and positive pressure. This supply of vacuum and positive pressure is controlled via the directional control valve 54 in combination with a positive pressure regulator 56 and a vacuum pressure regulator 58. The positive and negative pressure regulators 56, 58 can be electronically controlled pressure regulators and can be controlled via communication with a controller 70, which may be a processor.

When the directional control valve 54 directs negative pressure to either of the second pumping chambers 38, the adjacent flexible membrane 34 deflects to enlarge the associated first pumping chamber 36 and thereby drawing blood into the first pumping chamber 36. When the directional control valve 54 subsequently directs positive pneumatic pressure to the second pumping chamber 38, the flexible membrane 34 deflects back to constrict the first pumping chamber 36, thereby expelling blood from the first pumping chamber 36. The inlet and outlet valves 42, 44 are opened and closed accordingly. The dual chambers 32 are both operated in this manner to pump blood through the branch lines 40, 43.

The dual chambers 32 can be operated in a dual capacity mode or in a parallel mode. In dual capacity mode, the directional control valve 54 provides the two gaseous ports 50 with positive pneumatic pressure at the same time, and with negative pneumatic (vacuum) pressure at the same time. The dual chambers 32 then move blood in phase with each other. In the parallel mode, the directional control valve provides the gaseous ports 50 with positive and negative pressure alternatively rather than simultaneously, the dual chambers 32 will move blood fully or partially out of phase with each other, depending on the degree to which the positive and negative pressures are out of phase with each other.

Pressure sensors 60, such as pressure transducers, can also be provided for measuring the fluid pressure within the dual chambers 32. More specifically, the pressure sensors 60 can be placed in fluid communication with the second chambers 38, for monitoring pressure therein, and in electrical communication with the controller 70, for providing signals indicative of the measured pressure to the controller 70. As discussed below, this data may be used for calculating hydraulic impedance in the arterial line 22 and/or in the venous line 24.

The dual chambers 32 are each configured to draw a steady, preset vacuum pressure of about 0 to about −275 mm/Hg, and to exert a steady, preset positive pressure, to expel body fluid, at a pressure of about 0 to about +350 mm/Hg.

Cycle times for a blood treatment protocol can range between about 3 seconds to about 30 seconds for one full cycle of vacuum and positive pressure. The maximum suitable cycle time for a given system can be selected to be a sufficiently short time period (e.g., from about 3 seconds to about 6 seconds) to avoid adverse effects from stagnation of the volume of fluid in the treatment unit during the vacuum (fill) portion of the cycle, such as settling, coagulation and adhesion of proteins, etc. to surfaces within the dialyzer 14.

Referring again to FIG. 1, flow sensors (e.g., arterial and venous flow sensors 72a, 72b) are disposed along the arterial and venous lines 22, 24. Suitable flow sensors include ultrasonic and optical detectors. The arterial and venous flow sensors 72a, 72b can be configured to measure the associated flow rate 5 to 15 times per second (e.g., 10 times per second). The flow sensors 72a, 72b, provide signals indicative of the flow rate of the blood in the associated fluid line. The signals can be provided to the controller 70, which can utilize the measured flow rates to control other elements in the blood circuit 20, such as the inlet and outlet valves 42, 44, the directional control valve 54, the pneumatic pressure source 30, and/or audible or visual warning devices.

Other components which interact with the blood circuit 20 include a source of fluid, such as a saline bag 80, which communicates with the arterial line 22 via a saline line 82 and a saline valve 84 in electrical communication with the controller 70. Additionally, an anticoagulant solution such as a heparin supply 90 may communicate with the arterial line 22 through a heparin line 92 and an anticoagulant pump 94 that is responsive to the controller 70. A saline bolus may be administered to the blood stream by briefly closing an upstream arterial blood valve 100 opening the saline valve 84 and continuing operation of blood pump 26, thus drawing in saline rather than blood into the circuit. The upstream arterial blood valve 100 and the saline valve 84 may then be returned to position for the pump to draw blood into the circuit and push the saline and blood through the dialyzer 14 and the venous blood line 24.

The dialysis system 10 can also be provided with memory 110 (e.g., non-volatile memory) adaptively coupled to the controller 70. The memory 110 can be any form of memory that retains stored values when external power is turned off. For example, such non-volatile memory components include hard disks, flash memories, battery-backed-up RAM, and other data storage devices. The memory 110 may store instructions which, when executed, perform the various implementations of the disclosed method.

The dialysis system 10 can also include a data entry device 112, such as a keyboard, touch-screen monitor, computer mouse, or the like. The dialysis system 10 further includes a display device 114, such as a read-out monitor, for displaying of operating values of the various individual components of the dialysis system 10. The dialysis system 10 can be provided with a power source 116, a battery back-up 117, and a clock/timer 118. The controller 70, memory 110, data entry device 112, and clock/timer 118 represent one configuration of a control system.

The controller 70 coordinates the operation of the dialysis system 10 by controlling the blood flow in the blood circuit 20, the dialysate flow in the dialysate circuit 16, and the flow of saline or heparin to the arterial line 22 via the saline and heparin lines 82 and 92, respectively. To achieve this, the controller 70 utilizes hardware and/or software configured for operation of these components and can include any suitable programmable logic controller or other control device, or combination of control devices. Thus, blood flow in the blood circuit 20 is controlled by operating the blood pump 26 and controlling the upstream arterial blood valve 100 and the down stream venous blood valve 102 in the arterial and venous lines 22, 24. Dialysate flow in the dialysate circuit 16 can similarly be controlled by operating a dialysate pump 18. The controller 70 is responsive to various input signals it receives, such as input signals from the arterial and venous flow sensors 72a, 72b, the pressure transducers 60, and the clock/timer 118. Additionally, the controller 70 can display system status, warnings, and various other treatment parameters, on the display device 114. That allows an operator to interact with the controller via the data entry device 112.

The dialysis system 10, via the controller 70, selects an appropriate pressure (e.g., via control of the pressure regulators 56, 58) to achieve a given blood flow rate, and can also measure the pressure inside the blood pump 26 via the pressure sensors 60. Because the dialysis system 10 measures the blood flow rate (via the flow sensors 72a, 72b), the characteristic hydraulic impedance (Z) of both the arterial line 22 and the venous line 24 can be determined. The hydraulic impedance can be calculated from the following formula:

$$Q = P/Z$$

where:
Q=fluid flow rate;
P=fluid pressure; and
Z=hydraulic impedance

The hydraulic impedance Z is a complex number given by $Z = R + jX$. R, the real part of the impedance, is the resistance of the fluid circuit, and X, the imaginary part of the impedance, is the reactance of the circuit. If there is compliance, such as when orifices or chambers are present in the fluid circuit, the flow rate Q does not change instantaneously with pressure P. The reactance X accounts for this lag between the flow rate Q and the pressure P. In some cases, such as when there is little compliance, the real part of the impedance dominates, and thus, for simplification, the impedance Z can be estimated as being substantially equal to the resistance R.

Causes of blood flow degradation, such as clots or occlusions or changes in access flow rate, can be inferred from the hydraulic impedance and/or from changes in the hydraulic impedance. Clots, occlusions, and reduced access blood flow rates can reduce clearance (i.e., the rate at which certain fluids and solutes are cleared from the blood) in hemodialysis patients. Detecting and identifying reductions in flow can allow these issues to be corrected to maintain clearance.

Identification of a cause of blood flow degradation can allow for correction of the issue before treatment efficacy is compromised. This can give an operator an opportunity to continue effective treatment in circumstances where treatment may have otherwise been compromised or abandoned.

Because of the ability of the dialysis system 10 to modulate pressure (via control of the pressure regulators 56, 58) to achieve a set flow, the pressure applied to arterial and venous blood is known. Because the arterial and venous blood flow is know, e.g., from the arterial flow sensor 72a and the venous flow sensor 72b, respectively, the arterial and venous flow resistance can be determined as follows:

$$Z_A = P_A/Q_A$$

$$Z_V = P_V/Q_V$$

Where:
$Z_A$=arterial line impedance;
$P_A$=arterial line pressure;
$Q_A$=arterial line flow rate;
$Z_V$=venous line impedance;
$P_V$=venous line pressure; and
$Q_V$=venous line flow rate By trending or comparing a current impedance value (i.e., the average value for a current cycle, either arterial or venous) to a baseline value (i.e., an arterial baseline value or a venous baseline value), the impedance of both the arterial line 22 and the venous line 24 can be monitored over time in order to detect degradations in the respective flow rates. The baseline values may be stored values (e.g., empirically pre-determined values stored in memory 110) and/or a moving ensemble average value (e.g., an average impedance value of some or all preceding cycles over a given period of time). Nominal increasing impedance may be expected due to normal hemoconcentration over time. However, excessive increases in impedance can be used to indicate clotting or access blockages.

A percentage increase in impedance in both the arterial line 22 and the venous line 24 for the current cycle can be calculated as follows:

$$\% \text{ increase arterial} = (Z_{A(current)} - Z_{A(baseline)})/Z_{A(baseline)}$$

$$\% \text{ increase venous} = (Z_{V(current)} - Z_{V(baseline)})/Z_{V(baseline)}$$

The percentage increase values can then be compared to maximum threshold values in order to determine whether the percentage increase in impedance is indicative of an issue contributing to the degradation of blood flow. These maximum threshold values for increases in the hydraulic impedance (arterial or venous) can be set and/or adjusted by an operator via the data entry device 112, or can be pre-stored in the memory 110.

The various issues that may contribute to degradation of blood flow include kinking in the arterial or venous tubing; a needle at the access point engaging (e.g., bumping up against) a sidewall of the patients vein; and clot formation, which often occurs at the inlet of the dialyzer 14. A kink in the tubing, for example, can be expected to produce a relatively large spike in the hydraulic impedance. For example, if a kink reduces blood flow by 90% the hydraulic impedance increases by about 10× proportional to the reduction in blood flow. If a needle bumps against the sidewall reducing the blood flow by 50% the impedance will increase by about 2× (200%) proportional to the blood flow. Clots at a flow reduced by 20% will yield an increase in impedance of about 1.25× (125%).

The location of a cause of blood flow degradation can be determined based on which of the flow sensors measured the increased impedance and the measured increased in hydraulic impedance. For example, a relatively large spike in the hydraulic impedance measured by the arterial flow sensor 72a may indicate a kink in the arterial line 22, whereas a relatively large spike in the hydraulic impedance measured by the venous flow sensor 72b may indicate a kink in the venous line 24. Similarly, an increase in the hydraulic impedance of about 20% measured by the arterial flow sensor 72a may indicate a clot formation in the arterial line 22, whereas an increase in the hydraulic impedance of about 20% measured by the venous flow sensor 72b may indicate a clot formation in the venous line 24. An increase in the hydraulic impedance of about 100% measured by the arterial flow sensor 72a may indicate an access issue at an arterial patient connector 13. Likewise, an increase in the hydraulic impedance of about 100% measured by the venous flow sensor 72b may indicate an access issue at a venous patient connector 15. Thus, not only can a cause of blood flow degradation be inferred, but also the relative location of that cause of blood flow degradation. If blood flow degradation is detected, notification can be provided to the operator, e.g., via the display device 114 or by sounding an audible alarm 120, to prompt the operator to remedy the issue, e.g., by repositioning needles, delivering saline bolus or rinse back, to restore the flow rate. The notification can provide an indication of the cause of the blood flow degradation (e.g., kink, access issue, clot, etc.), as well as the location (e.g., arterial or venous line 22, 24) of the cause of the blood flow degradation. For example, if a kink in the tubing of the arterial or venous line 22, 24 is detected, a corresponding visual and/or audible alarm can be activated to notify the operator of the issue. The operator can then un-kink the arterial or venous line 22, 24 to restore the blood flow. If an access issue at the arterial or venous patient connector 13, 15 is detected, a corresponding visual and/or audible alarm can be activated to notify the operator of the access issue. The operator can then reposition the needle of the arterial or venous patient connector 13, 15 to restore the blood flow. If a clot in the arterial or venous line 22, 24 is detected, a corresponding visual and/or audible alarm can be activated to notify the operator of the clot, and the operator can then deliver heparin or saline to the arterial or venous line 22, 24 to clear the clot and restore blood flow.

Other Implementations

While certain implementations have been described above, other implementations are possible.

As an example, while implementations have been described in which, in response to the detection of blood flow blow degradation, the operator is prompted to perform an action to restore blood flow, in some implementations, the dialysis system 10 can be configured to remedy the cause of the blood flow degradation automatically. For example, the dialysis system 10 can be configured to automatically administer a saline bolus or anticoagulant solution, e.g., via operation of the controller 70, where, for example, a clot is detected.

Figure 3:
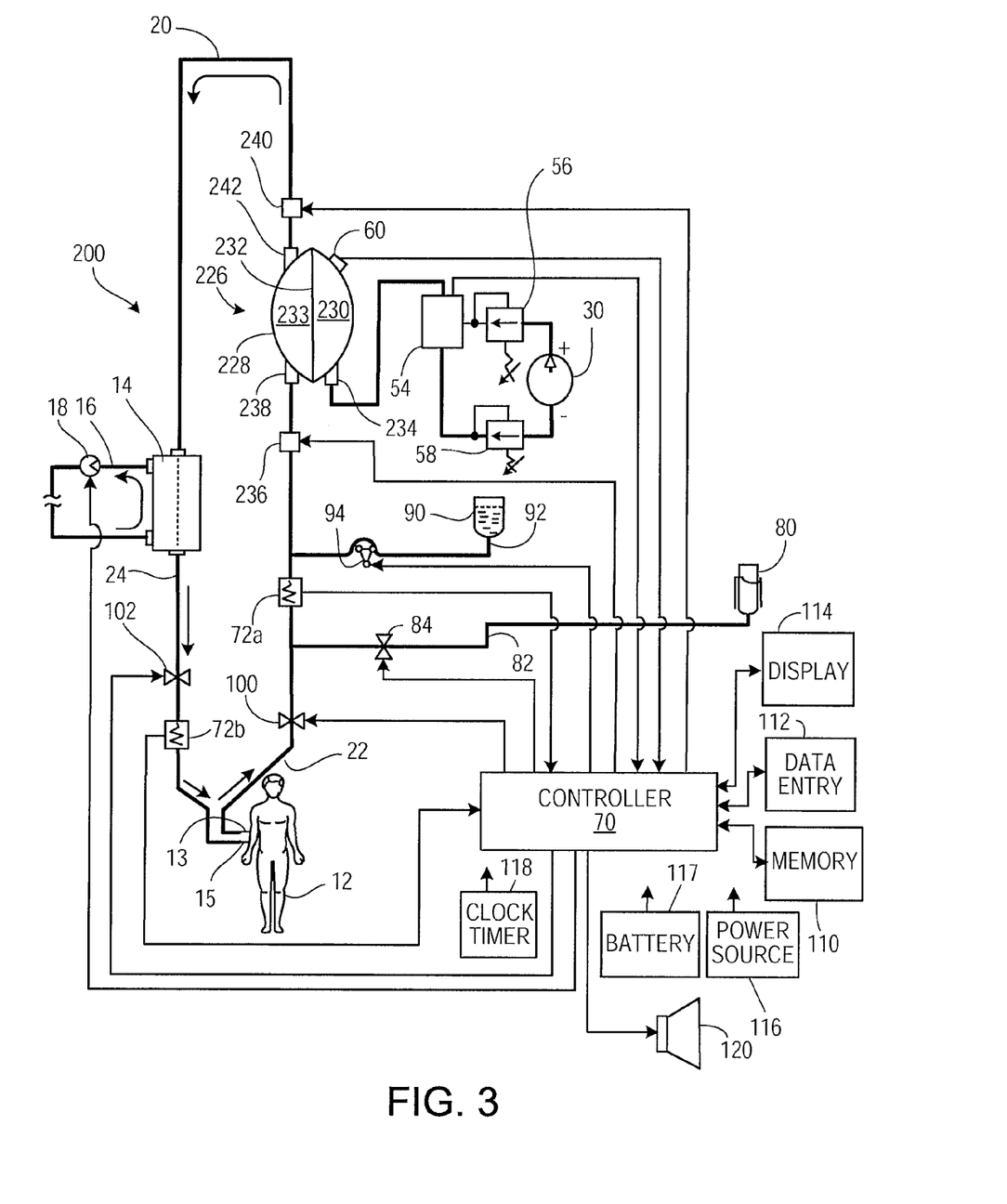
FIG. 3 is a schematic view of a dialysis system that has a single chamber blood pump.

While a dialysis system having a dual chamber blood pump has been described, in some implementations, the blood pump may instead include a single chamber device. For example, FIG. 3 illustrates a dialysis system 200 that includes a single chamber blood pump 226. The single chamber blood pump 226 includes an outer housing 228 defining a pneumatic chamber 230 and a flexible membrane 232 defining a blood chamber 233. The outer housing 228 includes at least one gaseous port 234, which is in fluid communication with a pneumatic pressure source 30 via a directional control valve 54. An inlet valve 236 provides for fluid communication between an arterial line 22 and an inlet port 238 of the blood chamber 233. An outlet valve 240 provides for fluid communication between an outlet port 242 of the blood chamber 233 and a venous line 24. As in the case of the dual chamber pump described above, the controller 70 controls blood flow in the blood circuit 20 via operation of the inlet and outlet valves 236, 240, the directional control valve 54 and/or the pneumatic pressure source 30.

Figure 4:
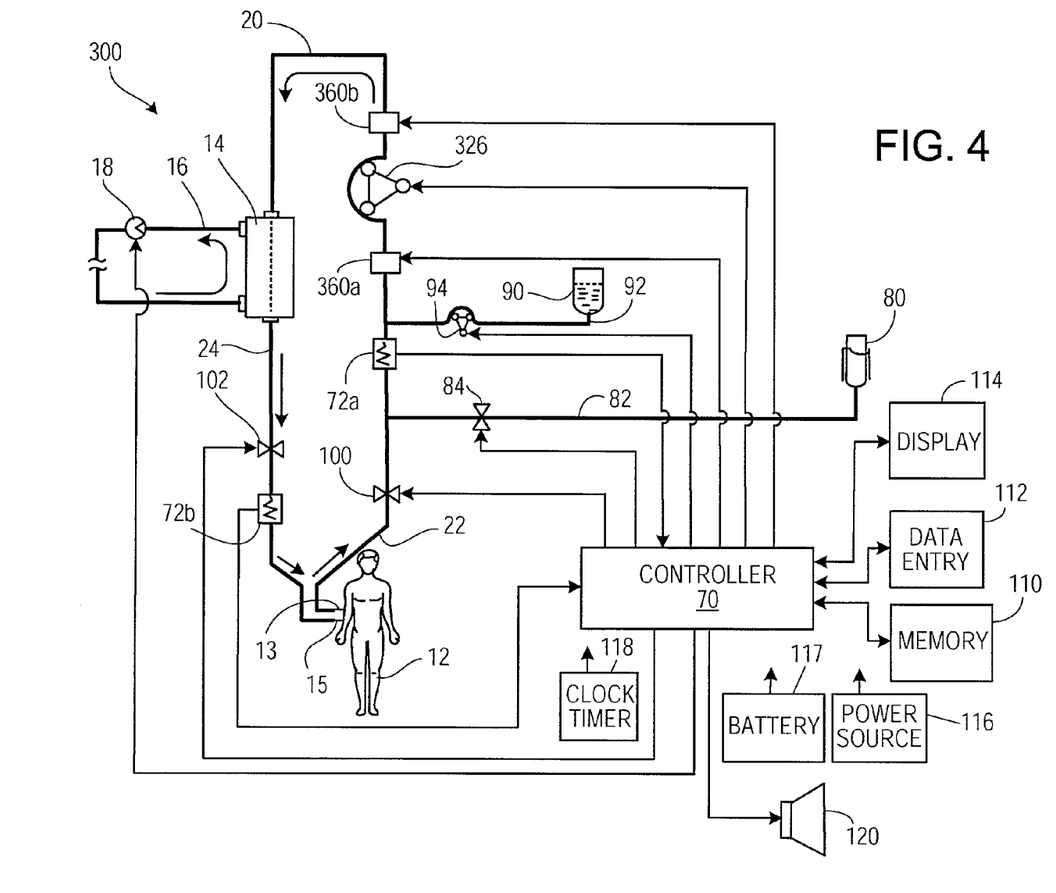
FIG. 4 is a schematic view of a dialysis system that has a peristaltic blood pump.

FIG. 4 illustrates another example of a dialysis system 300 which utilizes a peristaltic pump 326 for pumping blood through the blood circuit 20. Arterial and venous pressure sensors 360a, 360b are provided for measuring pressure of blood flowing through the arterial and venous lines 22, 24, respectively. The arterial and venous pressure sensors 360a, 360b provide signals indicative of the measured pressures to the controller 70, which utilizes the pressure data, along with blood flow rate data measured by arterial and venous flow rate sensors 72a, 72b, to calculate the hydraulic impedances in the arterial and venous lines 22, 24. Alternatively or additionally, when using a peristaltic pump, the flow can be inferred directly from the pump speed because the pump is a fixed flow device.

Figure 5:
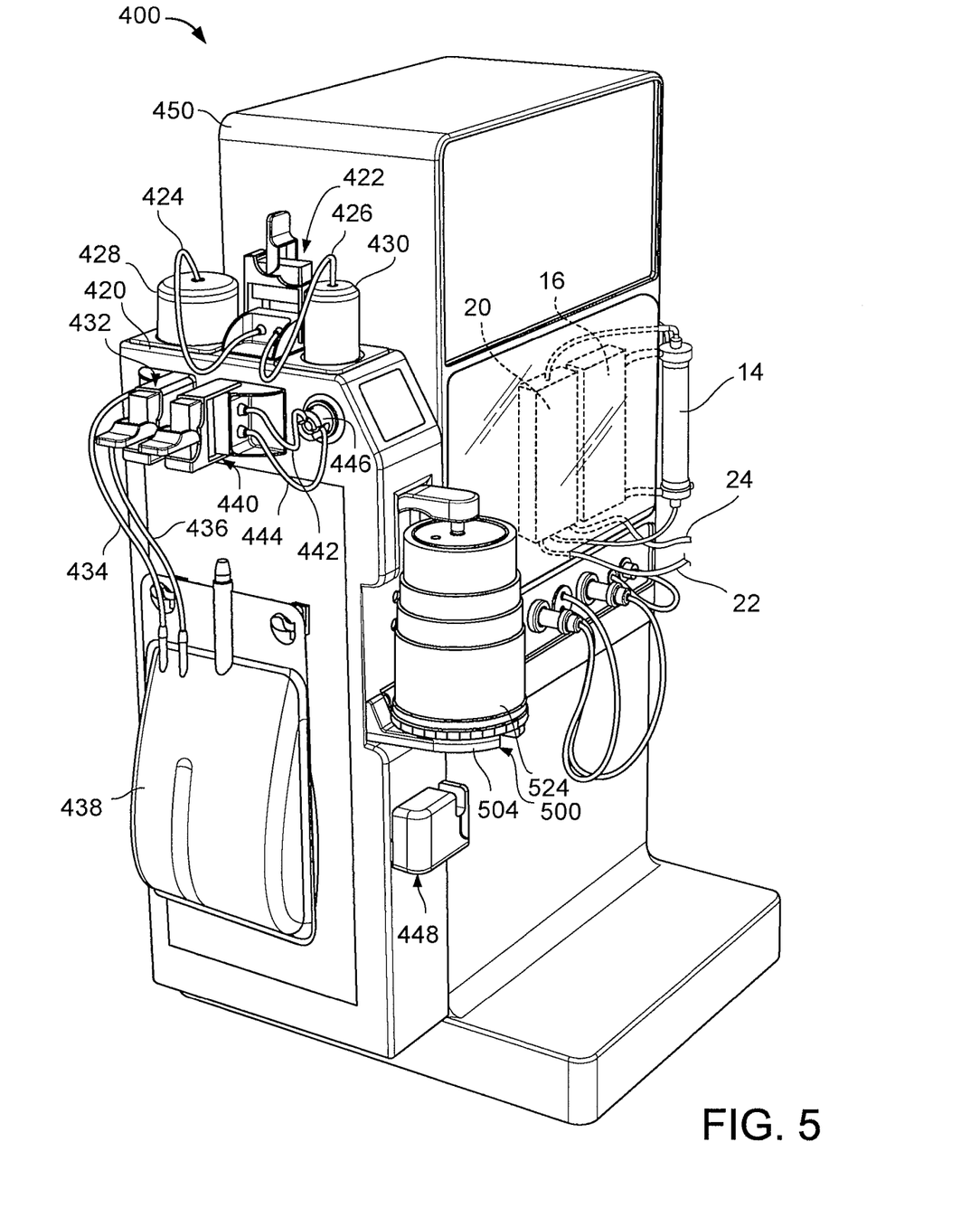
FIG. 5 is a perspective view of a dialysis system that includes a dialysis machine and a module with a sorbent cartridge holder that is holding a sorbent cartridge.

In some cases, the methods for detecting blood flow degradation described above can also be incorporated in sorbent-based dialysis systems. FIG. 5 shows a sorbent-based dialysis system 400 that includes a module 420 fluidly coupled to a dialysis machine 450, which houses a blood circuit 20 and a dialysate circuit 16 such as described above, e.g., with reference to FIG. 1. The module 420 includes a sorbent cartridge holder 500 configured to hold a sorbent cartridge 524. The module 420 also includes a manifold 422 to which fluid lines 424, 426 extending from an infusate container 428 and a sodium chloride container 430 are connected, a manifold 432 to which fluid lines 434, 436 extending from a dialysate bag or reservoir 438 are connected, and a manifold 440 to which fluid lines 442, 444 extending from an ammonium ($NH_4$) sensor 446 are connected. The module 420 further includes a manifold 448 that can be used to fluidly connect other components, such as a priming solution bag, a rinsing solution bag, a cleaning solution bag, and/or a drain bag to the module 420. Each of manifolds 422, 432, 440, and 448 can, for example, include projections on which fluid lines can be positioned to connect the various components described above to their respective manifold. Any of various other suitable connection mechanisms can alternatively or additionally be used to connect the fluid lines to the manifolds.

When in an open position, as shown in FIG. 5, the manifold 422 permits an infusate solution (e.g., a solution including magnesium, calcium, and potassium) and a sodium chloride solution to be delivered into fluid circulating through the module 420. Pumps and valves within the module 420 can, for example, be activated to pump the infusate solution and sodium chloride into the fluid circulating within the module 420. Similarly, the manifold 432 allows fluid to be transferred from the module 420 to the bag 438 and vice versa. Using pumps and valves within the module 420, fluid can be pumped into and suctioned out of the bag 438 via the fluid line 434 connected to the manifold 432. The manifold 440 permits fluid to be transferred from the module 420 to the ammonium sensor 446 and vice versa. By activating pumps and valves within the module 420 in a desired manner, the fluid can be pumped from the module 420 to the ammonium sensor 446 and can be drawn back to the module 420 from the ammonium sensor. The manifold 448 can also be placed in an open configuration during use and connected to fluid lines such that by activating pumps and valves within the module, fluid can be drawn into the module 420 from a bag (e.g., a priming solution bag, a rinsing solution bag, a cleaning solution bag) and/or pumped from the module into a bag (e.g., a drain bag). With the sorbent cartridge 524 fluidly connected to the cartridge holder 500, as shown in FIG. 5, fluid circulating within the module 420 is allowed to pass through the sorbent cartridge 524.

During dialysis treatment, the module 420 is configured in the manner shown in FIG. 5 to permit fluid communication between the fluid circulating within the module 420 and the sorbent cartridge 524, the infusate container 428, the sodium chloride container 430, the dialysate bag 438, the ammonium sensor 446, and, in some cases, one or more additional bags that can be connected to the module 420 via the manifold 448.

During dialysis treatment, spent dialysis solution is moved from a dialysate circuit 16 (FIG. 1) of the dialysis machine 450 into the module 220 where it passes through the sorbent cartridge 524, and then the recycled dialysis solution exiting the sorbent cartridge 524 is moved back to the dialysis machine 450. As the spent dialysis solution is passed through the sorbent cartridge 524, toxins, such as urea, and other substances, such as calcium, magnesium, and potassium are stripped from the spent dialysis solution. Sodium can also be stripped from the spent dialysis solution or, in certain cases, added to the spent dialysis solution as the spent dialysis solution passes through the sorbent cartridge 524. Thus, calcium, magnesium, potassium, and sodium levels of the recycled dialysis solution exiting the sorbent cartridge 524 can be altered (e.g., by introducing calcium, magnesium, potassium, sodium, and/or a diluent into the recycled dialysis solution) to restore concentrations of those substances to desired levels. As the recycled dialysis solution then passes through a dialyzer 14 (FIG. 1) in the dialysis machine 450, toxins are transferred from the patient's blood into the dialysis solution, forming spent dialysis solution. This spent dialysis solution is then circulated through the module 420 again to recycle or regenerate the spent dialysis solution. This process can be repeated until a desired amount of toxins have been removed from the patient's blood. Because the dialysis solution is recycled during the treatment as opposed to simply being discarded, the volume of dialysis solution used during the treatment can be substantially reduced relative to certain conventional hemodialysis techniques. In addition, maintaining the concentration of the various substances within the dialysis solution, such as calcium, magnesium, potassium, and sodium, can help to prevent the patient from experiencing discomfort during the treatment. As with the system described above, e.g., with reference to FIG. 1, flow sensors and pressure sensor can be positioned along the blood circuit 20 of the dialysis machine 450, and measurements from the sensors can be used for the detection and identification of blood flow degradation, and causes thereof, such as clots, occlusions, and access blockage, within the dialysis system.

While methods for detecting blood flow degradation in dialysis systems have been described, the methods may also be employed in other types of extracorporeal blood treatment systems.

Other implementations are within the scope of the following claims.

What is claimed is:

1. A method for detecting blood flow degradation in a dialysis system, the method comprising:
    calculating a current impedance value based on measured data, the measured data corresponding to a property of blood in a blood line;
    comparing the current impedance value to a baseline impedance value; and
    determining a cause of blood flow degradation indicated by the difference between the current impedance value and the baseline impedance value.

2. The method of claim 1, further comprising inferring blood flow degradation if the current impedance value differs from the baseline impedance value by more than a maximum limit.

3. The method of claim 1, further comprising:
    transmitting a signal corresponding to the measured data to a controller; and
    utilizing the controller to calculate the current impedance value based on the measured data.

4. The method of claim 3, further comprising utilizing the controller to compare the current impedance value to the baseline impedance value.

5. The method of claim 1, further comprising alerting a user if the current impedance value differs from the baseline impedance value by more than a maximum limit.

6. The method of claim 5, wherein alerting the user comprises activating an alarm.

7. The method of claim 6, wherein the alarm is an audible alarm.

8. The method of claim 6, wherein the alarm is a visual alarm.

9. The method of claim 5, wherein alerting the user comprises displaying information concerning a detected blood flow degradation on a display device.

10. The method of claim 9, wherein the displayed information comprises information regarding a cause of blood flow degradation.

11. The method of claim 9, wherein the displayed information comprises information regarding a location of a cause of blood flow degradation relative to the dialysis system.

12. The method of claim 1, further comprising administering a saline bolus if the current impedance value differs from the baseline impedance value by more than a maximum limit.

13. The method of claim 12, wherein the saline bolus is automatically administered at the direction of a controller of the dialysis system.

14. The method of claim 1, further comprising adjusting a needle at a patient access point if the current impedance value differs from the baseline impedance value by more than a maximum limit.

15. The method of claim 1, further comprising un-kinking kinked tubing if the current impedance value differs from the baseline impedance value by more than a maximum limit.

16. The method of claim 1, further comprising determining a location of a cause of blood flow degradation based, at least in part, on the difference between the current impedance value and the baseline impedance value.

17. The method of claim 1, wherein comparing the current impedance value to the baseline value comprises calculating a percent difference between the current impedance value and the baseline value.

18. The method of claim 17, wherein identifying the cause of blood flow degradation is based on the calculated percent difference.

19. A computer-readable medium having encoded thereon software for detecting blood flow degradation in a blood circuit, the software comprising instructions for:
    receiving information corresponding to measurement data from one or more sensors;
    calculating a current impedance value based on the measurement data;
    comparing the current impedance value to a baseline impedance value; and
    determining a cause of blood flow degradation indicated by the difference between the current impedance value and the baseline impedance value.

20. The computer readable medium of claim 19, wherein the software further comprises instructions for calculating the baseline impedance value based, at least in part, on measurement data received from the one or more sensors.

21. A dialysis system comprising:
    a blood circuit comprising:
        a blood pump,
        tubing for conveying blood between the blood pump and a patient;
    one or more sensors for measuring a property of blood within the tubing; and
    a controller in communication with the one or more sensors and configured to calculate a hydraulic impedance within the tubing based, at least in part, on signals received from the one or more sensors.

22. The dialysis system of claim 21, wherein the tubing comprises an arterial line for conveying blood from a patient to the blood pump, and a venous line for conveying blood from the pump back to the patient.

23. The dialysis system of claim 22,
wherein the one or more sensors comprise an arterial flow sensor arranged to measure a flow rate of blood flowing within the arterial line, and
wherein the controller is configured to calculate a hydraulic impedance within the arterial line based, at least in part, on signals received from the arterial flow sensor.

24. The dialysis system of claim 22,
wherein the one or more sensors comprise a venous flow sensor arranged to measure a flow rate of blood flowing within the venous line,
wherein the controller is configured to calculate a hydraulic impedance within the venous line based, at least in part, on signals received from the venous flow sensor.

25. The dialysis system of claim 21,
wherein the one or more sensors comprise one or more pressure sensors for measuring pressure within the tubing, and
wherein the controller is in communication with the one or more sensors.

26. The dialysis system of claim 21, wherein the controller is configured:
to compare the calculated hydraulic impedance to a baseline impedance value, and
to detect a blood flow degradation based on the comparison.

27. The dialysis system of claim 21, further comprising a display device in communication with the controller, wherein the controller is configured to display information concerning a detected blood flow degradation on the display device.

28. The dialysis system of claim 21, further comprising an audible alarm, wherein the controller is configured to sound the audible alarm in response to detecting a blood flow degradation.

29. The dialysis system of claim 21, wherein the controller is configured to control operation of the pump, and wherein the controller is configured to halt operation of the pump in response to detecting a blood flow degradation.

30. The dialysis system of claim 21, further comprising:
a saline source,
a saline line connecting the saline source to the tubing, and
a saline valve in electrical communication with the controller,
wherein the saline valve is operable to control a flow of saline from the saline source toward the tubing, and
wherein the controller is configured to administer a saline bolus, via operation of the saline valve, in response to detecting a blood flow degradation.

31. The dialysis system of claim 21, further comprising memory in communication with the controller.

32. The dialysis system of claim 31, wherein the memory includes stored data corresponding to a baseline impedance value.

33. The dialysis system of claim 31, wherein the controller is configured:
to calculate a baseline impedance value based, at least in part, on signals received from the sensors, and
to cause the baseline impedance value to be stored in the memory.

34. The dialysis system of claim 21, wherein the blood pump is a peristaltic pump.

35. The dialysis system of claim 21, further comprising a dialyzer, connected to the blood circuit, for separating waste from blood flowing within the blood circuit.

36. The dialysis system of claim 21, further comprising a dialysate circuit through which dialysate flows.

37. The dialysis system of claim 36, further comprising a sorbent cartridge in fluid communication with the dialysate circuit and configured so that the dialysate can pass therethrough, the sorbent cartridge being adapted to remove one or more substances from the dialysate as the dialysate passes through the sorbent cartridge.

38. The dialysis system of claim 21, wherein the dialysis system is a hemodialysis system.

39. The dialysis system of claim 21, wherein the dialysis system is a sorbent-based dialysis system.

40. The method of claim 1, wherein the measured data corresponds to a flow rate of blood in the blood line.

41. The method of claim 1, wherein the measured data corresponds to a pressure of blood in the blood line.

42. The method of claim 1, wherein the base line impedance value corresponds to an average impedance value of at least some preceding dialysis cycles over a given period of time.

43. The computer readable medium of claim 19, wherein the software further comprises instructions for calculating the baseline impedance value as an average impedance value of at least some preceding dialysis cycles over a given period of time.

44. The dialysis system of claim 26, wherein the base line impedance value corresponds to an average impedance value of at least some preceding dialysis cycles over a given period of time.

45. The dialysis system of claim 21, wherein the controller is configured to determine a likely cause of blood flow degradation indicated by the difference between the current impedance value and a baseline impedance value.

46. The method of claim 1, wherein if the difference between the current impedance value and the baseline impedance value corresponds to an increase in the current impedance value of about 20 to 25 percent, a cause of blood flow degradation is determined to be clot formation.

47. The method of claim 1, wherein if the difference between the current impedance value and the baseline impedance value corresponds to an increase in the current impedance value of about 100 percent, a cause of blood flow degradation is determined to be at least partial occlusion of an access needle of a blood line.

48. The method of claim 1, wherein if the difference between the current impedance value and the baseline impedance value corresponds to an increase in the current impedance value of about 500 percent, a cause of blood flow degradation is determined to be a kink in a blood line.

* * * * *